Figure 1A:
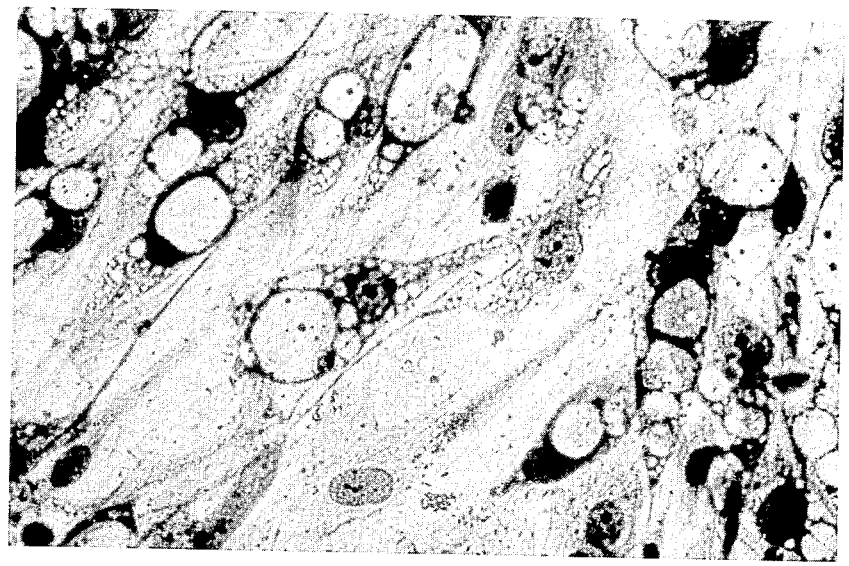

United States Patent [19]

Kopelovich

[11] Patent Number: 4,735,895
[45] Date of Patent: Apr. 5, 1988

[54] CANCER SUSCEPTIBILITY TEST

[75] Inventor: Levy Kopelovich, St. Petersburg, Fla.

[73] Assignee: Oncotech, Inc., Wilmington, Del.

[21] Appl. No.: 687,047

[22] Filed: Dec. 28, 1984

[51] Int. Cl.$^4$ .................. C12Q 1/02; C12Q 1/32
[52] U.S. Cl. .................................... 435/5; 435/26; 435/29; 435/240.23; 436/813
[58] Field of Search .............. 435/5, 240, 26, 240.23, 435/29; 436/813

[56] References Cited

U.S. PATENT DOCUMENTS

| | | | |
|---|---|---|---|
| 4,529,693 | 7/1985 | Smith | 436/813 X |
| 4,532,220 | 7/1985 | Lavi | 436/813 X |
| 4,535,058 | 8/1985 | Weinberg | 436/813 X |
| 4,582,787 | 4/1986 | Frankel | 435/5 |

OTHER PUBLICATIONS

Chemical Abstracts, 100:63293b (1984).
Rhim, J. S., Proc. Soc. Exp. Biol. Med., 174(2), 217-223 (1983).
Wise, L. S. et al., J. Biol. Chem. 254(2), 273-275 (1979).
Pfeffer and Kopelovich, 1977, Cell 10:313-320.

Primary Examiner—Sidney Marantz
Attorney, Agent, or Firm—Pennie & Edmonds

[57] ABSTRACT

The present invention relates to an improved viral transformation/neodifferentiation assay for determining predisposition to cancer. The invention is based on the association between retroviral transformation/neodifferentiation and a predisposition to cancer. The level of lipogenic enzymes is measured in cultured human fibroblast cells after transformation/neodifferentiation with Kirsten murine sarcoma virus in the presence of glucocorticosteroids to monitor the extent of conversion of the human skin fibroblasts to fully mature adipocytes.

13 Claims, 1 Drawing Sheet

CANCER SUSCEPTIBILITY TEST

TABLE OF CONTENTS
1. FIELD OF THE INVENTION
2. BACKGROUND OF THE INVENTION
   2.1 TERMINOLOGY
   2.2 PREDISPOSITION TO CANCER
   2.3 STRATEGIES FOR THE DETECTION OF CANCER SUSCEPTIBILITY.
   2.4 PROTO-ONCOGENES AND ONCOGENES
   2.5 RELATIONSHIP BETWEEN CANCER AND ONCOGENIC VIRUSES
   2.6. DIFFERENTIAL SUSCEPTIBILITY TO TRANSFORMATION BY ONCOGENIC VIRUSES
   2.7. CHARACTERIZATION OF KIRSTEN MURINE SARCOMA VIRUS (KiMSV)
3. SUMMARY OF THE INVENTION
4. BRIEF DESCRIPTION OF THE FIGURES
5. DESCRIPTION OF THE INVENTION
   5.1. TISSUES
   5.2. VIRUS PREPARATION
   5.3. VIRAL TRANSFORMATION AND DETERMINATION OF CANCER SUSCEPTIBILITY
6. Example: CANCER SUSCEPTIBILITY
   6.1. SKIN BIOPSY SOURCES
   6.2. SKIN FIBROBLAST CULTURES
   6.3. PREPARATION OF KIRSTEN MURINE SARCOMA VIRUS (KiMSV)
   6.4. VIRAL INFECTION
   6.5. TRANSFORMATION ASSAY
   6.6. MEASUREMENT OF GLYCEROPHOSPHATE DEHYDROGENASE AS DIFFERENTIATION MARKER

1. FIELD OF THE INVENTION

The present invention relates to a diagnostic test for individuals predisposed to cancer. The invention is based on the association between the increased sensitivity of human skin fibroblasts (SF) to transformation by oncogenic viruses and predisposition to cancer in otherwise apparently healthy individuals. Specifically, the present invention demonstrates the use of markers of cell transformation/neodifferentiation induced by an RNA virus, the Kirsten murine sarcoma virus (KiMSV), to monitor the extent of transformation/neodifferentiation of human skin fibroblasts to adipose cells by KiMSV. The more sensitive the cells are to transformation/neodifferentiation by KiMSV, the greater the probability that a person from whom such cells have been derived will be prone to develop cancer.

The method of the present invention is demonstrated through the correlation between several independent parameters including: (1) measurement of lipogenic enzymes associated with transformation/neodifferentiation of human SF to adipose cells by KiMSV in the presence of a glucocorticoid hormone; and (2) measurement of morphological changes as seen through staining with tissue specific dyes. These parameters are easily assayed in the laboratory using currently available automated equipment. Thus, this screening test can be used in vitro for clinical diagnostic purposes for detection of predispositon to cancer.

2. BACKGROUND OF THE INVENTION

2.1. TERMINOLOGY

For the purposes of this invention the terminology and basic concepts used are defined as described below.

Skin fibroblasts (SF) are derived from connective tissue of the skin. Adipose cells (also referred to as adipocytes or fat cells) are cells with little cytoplasmic volume that possess large vacuoles containing triglycerides and are usually derived from adipose tissue.

The term "cell genotype" describes the genetic constitution of a cell.

The term "cell phenotype" or "phenotypic expression" describes the appearance or other characteristics of a cell resulting from the interaction between its genetic constitution and the environment.

The term "transformation/neodifferentiation" or "transformed/neodifferentiated cell" is used to connote the occurrence of a change from a fully differentiated normal cell type to a new cell phenotype; this may occur in vivo or in vitro. This change may be complete, i.e., the conversion of a fully differentiated cell type into a newly differentiated fully mature cell type, or it may be partial, i.e., representing various stages along the transformation/neodifferentiation process. The occurrence of abnormal phenotypic expressions during such a transition can be monitored in vitro.

The term "cancer predisposition" is used to describe the transformed/neodifferentiated phenotype when a discussion about in vivo susceptibility mechanisms is indicated. Predisposition to cancer suggests the higher than average occurrence of cancer in certain population groups. Cancer predisposition appears to be due to the interaction of genetic and environmental factors. In some instances, however, cancer predisposition can be described as primarily constitutive (genetic), while in others it is apparently principally environmentally induced.

The terms "neoplasia" and "tumor" will be qualified, where necessary, as benign or maglignant. All other synonyms for cancer are used to mean a tumor which is malignant by the usual criteria in vivo, i.e., a tissue which grows progessively and which, if left untreated, will kill the host organism.

The term "autosomal dominant cancer trait" is used to describe susceptibility alleles perceived through a statistical analysis of various genetic models. For example, in a pattern of inheritance involving autosomal dominant genes in which one parent is heterozygous (T/t) for an autosomal dominant gene (T) and the other parent is homozygous for the normal allele (t/t), each child (T/t $\times$ t/t) has a 50 percent chance of receiving the abnormal allele T, thus being affected, and a 50 percent chance of receiving the normal allele t, thus being normal. Hence, on the average, half of the children will have the trait. (For a more complete discussion of this topic see Thompson and Thompson, in *Genetics in Medicine*, 1973, W. B. Saunders Company, Philadelphia, pp. 48–88).

2.2. PREDISPOSITION TO CANCER

In order to identify the molecular events that effect a change from normal to malignant cells, the nature of the genetic determinants associated with transformation in vitro and tumorigenicity in vivo need to be considered. It is generally believed that all forms of cancer are due to heritable and permanent changes in the cell genome.

A view that considers cancer as an expression of a particular state of differentiation (epigenetic) rather than as a genetic variant has also been proposed. Conceivably, both genetic and epigenetic mechanisms are associated with the initiation and maintenance of the malignant state.

Cancer traits are presumably expressed through a class of normal differentiation genes which become either derepressed or amplified during the neoplastic process giving rise to cells which are predisposed to cancer. The phenotypic characterization of these cells can be used as a measure of the extent to which a cell differs from its normal phenotype, i.e., transformation/-neodifferentiation. Indeed, the transformation neodifferentiatior process observed in vitro in the laboratory is correlated with cancer predisposition in vivo. This has been repeatedly demonstrated for heritable forms of cancer.

An autosomal dominant pattern has also been recognized in a large number of familial aggregates predisposed to various forms of cancer. These comprise a large segment of all cancers reported worldwide. Additionally a strong genetic component also exists in the sporadic forms of cancer, i.e., in a general population, where such expression would be consistent with a dominant trait, albeit with only partial penetrance. For example, a recent study of over 1350 patients, representing a variety of primary cancers demonstrated that a familial tendency to develop cancer exists in the general population of cancer patients (Schneider et al., 1983, Am. J. Hum. Genet. 35: 454–467).

Thus a predisposition to cancer appears to be essentially similar qualitatively in the autosomal dominant cancer syndromes, the familial cancer syndromes, and the sporadic forms of cancer. Quantitative differences, however, could occur due to a gene dosage effect at the primary locus (cancer mutation) and at ancillary loci which modulate the expression of malignancy. An underlying assumption in many ongoing studies is that the site of this mutation in nonhereditary cancers is similar to that in hereditary cancers for the same type of cancer.

2.3. STRATEGIES FOR THE DETECTION OF CANCER SUSCEPTIBILITY

To date, several transformation-related abnormal phenotypic expressions have been used to identify individuals at a high risk for cancer. Examples of these abnormal phenotypic expressions include: (1) cellular expressions in an otherwise unperturbed cell, e.g., growth control and nutrient requirements, cytoskeletal and cytoplasmic membrane architecture, proteolytic activity, isozymic and antigenic profiles; (2) cellular expressions related to the sensitivity of cells to transformation by oncogenic viruses and by physical and chemical carcinogens, e.g., toxicity, clastogenic effects (apparent changes in chromosome structures) and the induction of a new cell phenotype.

The major strategies used for determining cancer predisposition are based on the use of a combination of tests on samples obtained by noninvasive procedures. Such noninvasive procedures include skin biopsies from clinically uninvolved skin and samples of lymphocytes, serum and urine. As a further aid in the identification of high-risk individuals, biopsy material can be obtained from a location close to a potential tumor site. This is done in cases in which medical history, family history or exposure to a specific environmental insult indicates a potential tumor site (e.g., breast, uterus, vagina, esophagus, rectal or lung tissue).

Although a combination of all available tests must be used, their specificity with regard to a certain cancer type should be established. Experience to date suggests that the use of exogenous, well-defined probes (e.g., virus, chemicals, etc.) on clinical material derived through noninvasive procedures increases the sensitivity of a potential cancer test considerably more than would be anticipated from the measurement of abnormal phenotypic expressions in unperturbed tissue samples. For example, an in vitro virus transformation test is available to diagnose individuals genetically at risk for certain types cf cancer. The currently used test, however, relies or the appearance of foci after viral transformation. Foci must be manually counted to give a relative index of genetic susceptibility to cancer. Another approach that has been suggested is to screen by karyotypic analysis for specific acquired chromosome defects following an insult by a clastogenic agent in the laboratory. For example, using this method a specific chromosome defect has been found to be associated with human small-cell lung cancer. All the current techniques, however, are time consuming and require more efficient assay procedures for application in the clinical laboratory. Thus, current tests to identify individuals predisposed to cancer suffer from two major disadvantages: insufficient sensitivity and/or inapplicability to currently available automated equipment in the clinical laboratory.

2.4 PROTO-ONCOGENES AND ONCOGENES

Oncogenes are genes that are intimately associated with cancer. They appear to be altered versions of normal genes (proto-oncogenes) encoding abnormal proteins which function to facilitate transformation of a normal cell into a cancer cell. The precise manner, however, by which proto-oncogenes become activated and their role in oncogenesis are not known. Oncogenes have been discovered in both retroviruses and in human cancer.

Studies with retroviruses (viruses whose genetic material is RNA which must be transcribed into DNA when the virus infects a eukaryotic cell) indicate that oncogenic retroviruses carry a single gene responsible for the induction of cancer in some cell systems. A variety of oncogenes have been isolated from retroviruses that cause carcinoma, sarcoma, leukemia or lymphoma in vertebrate species. These oncogenes are closely related to a normal gene in the host animal and encode an oncogenic protein similar to the host-cell protein.

Oncogenes are not actually viral genes, rather they are believed to be of cellular origin. The normal proto-oncogenes (e.g., $C\text{-}ras^{Ha}$, $C\text{-}ras^{Ki}$) are presumably acquired by a weakly oncogenic retrovirus during infection. The proto-oncogene may also become activated in normal cells undergoing oncogenesis by a variety of mechanisms. In fact, experiments have revealed that some oncogenes from spontaneously occurring human tumors are closely related to the oncogenes carried by several retroviruses. For example, the oncogene information found in the Kirsten murine sarcoma virus has been also found to be expressed in a large number of human carcinomas. Furthermore, DNA from human tumors introduced by transfection into NIH/3T3 murine cells can transform these cells into cancerous cells.

2.5. RELATIONSHIP BETWEEN CANCER AND TRANSFORMTION OF HUMAN CELLS BY ONCOGENIC VIRUSES

Recent evidence supports the view that protooncogenes contained in the genome are involved in the malignant transformation of normal human cells presumably through their effect on normal, tissue-specific differentiation genes. This evidence is based, in part, on the identification and isolation of DNA sequences and RNA transcripts from human cells which show homology with transforming genes of tumor viruses and on the transforming activity of such genes in the NIH/3T3 transfection assay. The abnormal expression of such genes may lead to a phenotypic change (transformation/neodifferentiation) which can induce cancer in affected cells. Activation of the tissue-specific differentiation genes, like that of the proto-oncogenes, might presumably occur oy derepression (dedifferentiation), or by transcriptional activation either through an increased number of gene copies (e.g., pseudogenes, carcinogen/promoter-induced aneuploidy), or through switching on of the gene(s) (spontaneous or induced). Conceptually, gene derepression has been interpreted in certain instances as the switch-on of an inactive differentiation gene(s) (an all or none phenomenon). Transcriptional activation on the other hand, is conceived primarily as a switch-up of gene expression from a normal, on-going level of expression to an abnormally high level of expression. For example, cell transformation is enhanced by transfection of cellular Murine sarcoma virus (MuSV) sequences ligated to the viral LTR (long-terminal repeat) sequence. Specific mutations, genetic fluidity of processed genes, and methylation patterns, represent additional mechanisms which are likely to be involved in malignant transformation. Presumably, several permutations of these processes might occur between one or more genes (a polygenic effect) to cause the synthesis of a gene product(s) whose presence in abnormally large amounts disrupts normal regulatory controls, ultimately leading to malignancy (gene-dosage).

Thus molecular-genetic considerations suggest that cancer associated genes (proto-cncogenes) may presumably activate normal differentiation genes; these represent different alleles of variable expressivity and involve a variety of susceptibility mechanisms. As such, however, the data available to date indicate that these genes cannot be used directly to distinguish individuals predisposed to cancer either qualitatively of quantitatively. The identification of a specific form of cancer, however, through restriction fragment length polymorphic probes, cytology, and indeed molecular biological tools, should be sought nevertheless.

It has been proposed, that predisposition to cancer can best be detected as a global syndrome at the phenotypic level (Kopelovich, in *Prevention of Hereditary Large Bowel Cancer*, 1983, Alan R. Liss, Inc. pp. 131-145). Properly selected biological and biochemical expressions, while presumably not specific for a given form of cancer, present the highest possible amplification level of the cancer trait. This approach faciliates the monitoring of interacting cancer gene(s) in all possible mutations as well as their modulation by other genes as it might occur in situ.

2.6. DIFFERENTIAL SUSCEPTIBILITY TO TRANSFORMATION BY ONCOGENIC VIRUSES

Perturbation of human cells by tumor viruses has been used to examine genetic determinants associated with cancer developments. Previous studies showed that cultured human fibroblasts from various sources differ in susceptibility to transformation by both RNA and DNA tumor viruses. Enhanced viral transformation of cultured skin fitroblasts (SF) has been demonstrated in individuals with certain autosomal dominant genetic disorders predisposing to cancer. For example, individuals with hereditary adenomatosis of the colon and rectum (ACR) and its variant, the Gardner Syndrome (GS), bilateral retinoblastoma (RB), and neurofibromatosis (NF), exhibit increased sensitivity to transformation/neodifferentiation by oncogenic viruses. In this respect, it is of interest that SF cultured from individuals with lung cancer in a general population are also more susceptible to transformation by KiMSV. SF from individuals with Huntington disease (Miller and Rasheed, 1981, Am. J. Hum. Genet. 33: 197-202), characterized by an autosomal dominant trait that *does not* predispose to cancer, however, are not abnormally sensitive to virus transformation/neodifferentiation.

Another indication of transformation/neodifferentiation by viruses is the presence of elevated levels of certain host-cell antigens. Thus, a class of transformation-related antigens, represented by the cell-coded p53 phosphoprotein, was found to form complexes with several tumor antigens. In addition, expression of the p53 protein is abnormally elevated in murine cell transformed by oncoviruses (both RNA and DNA), and by chemical and physical agents. Indeed, the level of expression of the p53 antigen appears to correlate with the extent of transformation/neodifferentiation of human skin fibroblasts by KiMSV. It is also overproduced in spontaneously occurring human tumor cells and in the serum of cancer patients.

The apparent sensitivity of cells from autosomal dominant syndromes which predispose to cancer to further transformation by oncogenic viruses (e.g., KiMSV, Adeno-12/SV40-hybrid) indicate that genetic information residing within these cells, probably in the form of a relatively limited and specific number of DNA sequences associated with the dominant gene(s) which contribute to each of these syndromes, renders them more sensitive to transformation by oncogenic viruses. Conceivably, the latter may be linked, in part, to overproduction of cell antigens such as p53. Thus while the exact role of retroviral oncogenes in malignant conversion is not clear, their specificity and utility as probes of cancer predisposition is nevertheless significant.

2.7. CHARACTERIZATION OF KIRSTEN MURINE SARCOMA VIRUS (KiMSV)

KiMSV belongs to the family of Retroviridae and is characterized by the presence of reverse transcriptase in the virions. The virions are enveloped, approximately 100 nm in diameter; the capsid is probably icosahedral and encloses the single stranded RNA genome. The mature virions are characterized by their appearance and are referred to as C particles because of the central core.

The Kirsten murine sarcoma virus (KiMSV) genome is a recombinant molecule derived from the Kirsten murine leukemia virus (KiMLV) genome and sequences transduced from a normal rat cell. (Norton and Avery, 1982, Biochem. Biophys. Res. Comm. 108:1631–1637). KiMSV is a replication defective, strongly oncogenic type C retrovirus. As with other retroviruses, linear and double standard DNA copies (proviruses) of the RNA genome are synthesized following infection of the host mouse cell with KiMSV. The linear DNA is approximately 6.5 kb and contains a long tandem repeat sequence (LTR) of 0.5 kb at each end.

Viral transformation of human cells by murine sarcoma virus (MSV) has been previously observed (Pfeffer and Kopelovich, 1977, Cell 10:313–320). The susceptibility to transformation by the Kirsten strain of MSV (KiMSV) varies according to the source of the individual cell strain and depends upon whether the cells were derived from a normal individual or an individual with genetic abnormalities or cancer. To date, in vitro transformation by the KiMSV has been identified and assayed by several characteristics. KiMSV transformed fibroblastic cultures generally lose the property of contact inhibition and hence form unorganized multilayers of cells. These cells then produce characteristic foci (colonies) over the normal resting cells. KiMSV transformed cells also from anchorage-independent colonies in a dose-dependant manner and, in numbers corresponding to the differential sensitivity of such cells for the virus at a given titer. In addition, host cell-coded antigens such as human fetal antigens have been used to monitor the extent of transformation/neodifferentiation of human SF by KiMSV.

Virus replication in infected human cultures is assayed in several ways. Detection of type C helper virus replication in KiMSV-infected cells is assayed by the XC synctial assay in which syncytial plaques are produced by the fusion of XC cells (rat cells transformed by RSV, Rous sarcoma virus) plated with cells infected by murine leukemia viruses. Virus can be identified by immunofluorescent plaques detected using fluorescent antibodies to group specific viral antigen. Virions may also be detected by measuring the RNA-dependent DNA polymerase activity, and by direct electron microscopy.

3. SUMMARY OF THE INVENTION

Prior to the present invention there has been no report of a reliable, practical and clinically rseful test for the detection of a predisposition to cancer. The present test can be used to detect predisposition to cancer in individuals constituitively sensitive to cancer, in individuals with a medical history or extensive family history of cancer and in individuals who might acquire cancer through repeated exposure to specific carcinogens in the environment. Individuals from the general populatior should also be included.

This invention is based on the proposition that predisposition to cancer can be detected as a global syndrome at the phenotypic level. In particular, the KiMSV virus transformation/neodifferentiation assay allows for the detection of biological and biochemical expressions associated with the induction of cancer in a variety of cancers.

The invention is based on the association between an increased sensitivity of human skin fibroblast (SF) to Kirsten Murine Sarcoma Virus (KiMSV) transformation/neodifferentiation and a predisposition to cancer. Identification of transformation/neodifferentiation-related phenotypic expressions in SF undergoing conversion to fully mature fat cells is used to detect individuals who are highly likely to develop cancer.

The present invention provides a novel diagnostic test for virus transformation/neodifferentiation of human SF to fat cells. This specific assay involves the determination of the level of enzyme activity of $\alpha$-glycerophosphate dehydrogenase (sn-Glycerol-3-phosphate: NAD+ 2-oxidoreductase, EC 1.1.1.8, herinafter referred to as glycerophosphate dehydrogenase or GDH) in virus transformed cells. The skin samples are cultured in vitro and cells grown from these cultures are transformed by the oncogenic virus KiMSV in the presence of glucocorticosteroid hormones including, but not limited to hydrocortisone, hydrocortisone 21-acetate, hydrocortisone 21-hemisuccinate, dexamethasone, etc. The addition of glucocorticosteroid hormone to the culture medium enables the virally transformed cells to develop the characteristics of fully differentiated fat cells and to exhibit an increase in lipogenic enzymes such as glycerophosphate dehydrogenase.

The present invention also contemplates monitoring the levels of other lipogenic enzymes for the detection of transformation/neodifferentiation by KiMSV. Concurrent with the monitoring of these enzyme levels, the invention further contemplates the testing of the cell cultures for the expression of the p53 antigen.

This assay is sensitive and specific for the detection of high levels of enzyme after viral transformation/neodifferentiation and addition of glucocorticosteroid hormone such as hydrocortisone. The test is simple and utilizes well known techniques. By using only cultured SF, a single cell type can be examined under reproducible conditions. The test can be readily performed by a person trained in the art. The relative ease of using this procedure should make it highly desirable as a standard screening procedure. There is an urgent need for such a test for the diagnosis of individuals at a high risk of cancer. In addition, the test is recommended to be used in follow up studies to predict the possibility that individuals who are "cured" of cancer may develop secondary neoplasms in the original target area and/or elsewhere.

The test may also be used as a genetic counseling device for diagnosing predisposition to cancer. It constitutes a valuable tool for providing a genetic basis to screen individuals at a high risk for environmertally-linked cancers, e.g., in industry. Such individuals would be advised to avoid particular chemical and physical agents in the environment that are presumably linked to the etiology of cancer.

The proper diagnosis of individuals at a high risk for cancer would lead to treatment and preventive therapy before the clinical onset of disease which should prove to be highly effective in controlling costs.

Finally, the invention provides methodologies useful in research for the study of cancer.

4. BRIEF DESCRIPTION OF THE FIGURES

Figure 1B:
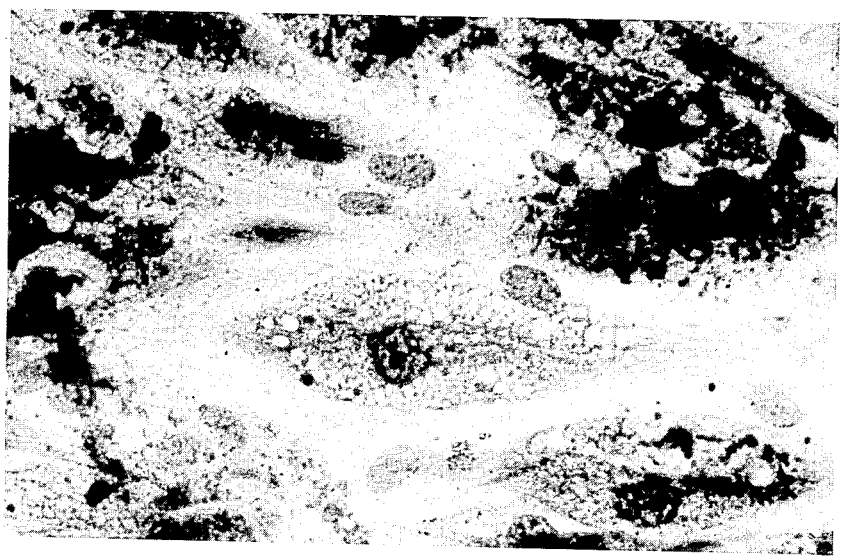

The present invention may be more fully understood by reference to the following detailed description of the invention, examples of specific embodiments of the invention, and the appended figure in which:

FIGS. 1 (A and B) represents the morphology of human skin fibroblasts undergoing transformation/neodifferentiation by KiMSV. Cell cultures were sequentially stained by the triglyceride-specific dye Oil-Red-O and then fixed and stained with Giemsa. The fat droplets stain orange-red with Oil-Red-O and they appear as empty vacuoles after fixation and staining with Giemsa. FIG. 1. illustrates transformation/neodifferentiation in the presence of 500 ng/ml hydrocortisone (100X magnification). FIG. 1B illustrates transformation/neodifferentiation in the absence of hydrocortisone (100X magnification). Differences in the size and distribution of the fat vacuoles and cytoplasmic volume in FIGS. 1 A and B are clearly apparent.

5. DESCRIPTION OF THE INVENTION

The present invention involves a diagnostic test for the detection of individuals predisposed to cancer. Skin fibroblasts derived from normal-appearing biopsies from individuals at risk of cancer are considerably more sensitive to transformation/neodifferentiation by the oncogenic virus KiMSV. Addition of a glucocorticosteroid hormone including but not limited to hydrocortisone, hydrocortisone 21-acetate, hydrocortisone 21-hemisuccinate, and dexamethasone, etc. to the culture medium in the presence of KiMSV produces cells that develop the characteristics of fully mature adipose cells. These cells possess large fat vacuoles and express elevated levels of lipogenic enzymes, including glycerophosphate dehydrogenase (GDH). The invention, therefore, is based on a correlation between predisposition to cancer and increased sensitivity of cultured human skin fibroblasts derived from such individuals to transformation/neodifferentiation to fat cells by KiMSV. This assay system can be used for diagnosis, and screening of a large number of individuals who are susceptible or at a high risk for cancer (e.g., those identified by epidemiological or occupational studies, and those individuals with a medical or family history of cancer), as well as those susceptible individuals who may be present in the general population.

A practical use for this test would include monitoring persons in industrial areas. Thus, persons involved in the automobile, petroleum, coal, or asbestos industries or individuals exposed to other chemical or physical agents associated with cancer would be periodically tested for an enhanced predisposition to cancer. Individuals found to be highly susceptible to cancer would be advised accordingly (e.g., to leave a particular environment; to avoid exposure to the harmful agents, or to modify behavior or occupation). With repeated monitoring, detection of the earliest clinical evidence of cancer is also possible. At that time, a prophylactic scheme would be adopted.

For the purpose of description, the method of the present invention can be divided into the following stages: (a) preparation of human cell cultures; (b) preparation of virus; (c) virus transformation; (d) enzyme assays; and (e) detection of antigen.

5.1 TISSUES

Human skin biopsies are obtained from clinically uninvolved skin. Indeed any other non-invasive procedures can be utilized, including but not limited to obtaining material from cells in the peripheral blood such as neutrophils, lymphocytes and moncocytes. If there is a genetic history of cancer in the family, if medical history indicates a potential tumor site, e.g., breast tissue; if there is a history of a particular cancer in the family e.g., breast cancer; if a person is employed in an industry which has been shown to be closely related to a specific type of cancer e.g., skin cancer; or if the individual uses contraceptives containing estrogens or progesterones which enhance the risk of particular cancers, e.g., vaginal, uterine, breast; or if an individual is a heavy smoker which enhances the risk of cancers such as lung, tongue, or cancer of the mouth biopsies may also be taken from the same individual in close proximity to the potential tumor site. This procedure is based on the fact that fibroblastic cells growing at a location adjacent to a primary tumor strongly express the transformed phenotype.

In a preferred embodiment of the present invention, human SF are obtained from subepidermoid biopsy specimens. These biopsy specimens are collected in a medium which provides a stable pH for transport of the tissue specimen to the clinical laboratory. Such specimens can be transported from *any* location and if necessary maintained for a period of 7 to 10 days before initiating the cultures. The tissue specimens are placed in a petri dish or flask and are minced with a surgical scalpel (primary explants). Monolayer cells from such primary explants are maintained in a defined medium such as Earle's balanced salt solution supplemented with glutamine, 1% sodium pyruvate and nonessential amino acids (EMEM) and 20% fetal bovine serum. A portion of these cells are frozen for later use and the remaining cells are used within the first 5-10 passages in culture as described below.

5.2 VIRUS PREPARATION

In a preferred embodiment, KiMSV is used to transform the cultured skin fibroblasts. Sufficient stocks of KiMSV for the present methods may be propagated in a cell line derived from normal rat kidney (NRK) (Klement et al., 1971, J. Nat. Cancer Inst. 47:65-73). To enhance the potency of virus preparation 2 ug/ml of hydrocortisone can be added to the tNRK cells during growth. Tissue culture fluid from subconfluent KiMSV-transformed NRK (tNRK) cells is harvested at 24 and 48 hours after the last medium change, clarified by slow speed centrifugation at 4° C. and stored under liquid nitrogen.

Large stocks of "reagent grade" virus each sufficient for the assay of at least $1 \times 10^6$ sample tests can be readily prepared. This will reduce variability between assays in different laboratories.

In alternative embodiments, a pseudotype of the KiMSV virus, such as the type C baboon endogenous virus (BaEV), other oncogenic viruses, a genetically engineered infectious agent or a synthetic product capable of effecting transformation of human cells may be used to transform the cultured SF. In addition, glucocorticosteroid hormones including but not limited to hydrocortisone, hydrocortisone 21-acetate, hydrocortisone 21-hemisuccinate and the synthetic glucocorticosteroid dexamethasone may be used to enhance transformation/neodifferentiation. It is essential that the glucocorticosteroid hormones used be better than 99 percent pure.

5.3 VIRAL TRANSFORMATION AND DETERMINATION OF CANCER SUSCEPTIBILITY

Viral transformation of the cultured SF is performed as follows. The SF cells growing in culture are incubated with diethylamineaminoethyl (DEAE) dextran for one hour and then infected with 10-fold serial dilutions of freshly-thawed, millipore filtered KiMSV stock virus with constant shaking for one hour. The virally infected cells are maintained in EMEM culture medium containing 10% fetal bovine serum and a glucocorticosteroid hormone such as hydrocortisone at 100-1000 ng/ml of for 14–21 days during which time the medium is changed every 3 days.

The number of foci, activity of lipogenic enzymes, and the level of p53 antigen can be determined at approximately 14–21 days following infection with the virus. Lipogenic enzymes which can be measured include, but are not limited to α-glycerophosphate dehydrogenase EC 1.1.1.8, GDH), glucose-6-phosphate dehydrogenase (G-6-PDH), malic enzyme citrate cleavage enzyme, acetyl-CoA carboxylase and fatty acid synthetase.

Cultures of the virally transformed cells are observed for focus formation using the following procedure. The transformed cells are exposed transiently to the dye Oil-Red-O and are then permanently fixed by Giemsa staining in order to detect the presence of fully mature fat cells. At the same time, cells from duplicate cultures are scraped off the flask, in the presence of ethylenediaminetetraacetic acid (EDTA) in an isotonic buffer. The cells are centrifuged at low-speed to remove cell nuclei and the supernatant is then centrifuged a second time at a higher speed to obtain the cytoplasmic fraction. The cytoplasmic content of the cells is then assayed for the activity of glycerophosphate dehydrogenase or other lipogenic enzymes. Elevated levels of cancer-related antigens such as p53 can be detected by immunoprecipitation with monoclonal antibody as described below.

The conversion or transformation/neodifferentiation of human SF by KiMSV and hydrocortisone appears to be more efficient at lower rates of cell proliferation. This can be achieved post-infection by lowering the concentration of serum in culture from 10% to 2–5% fetal bovine serum.

Furthermore, since serum constitutes a complex mixture of hormones, growth factors, transport proteins and nutrients and the actual amounts present in serum lots may differ it may be useful to standardize the components of the medium. It is now possible to grow the cells in medium containing artificially produced serum such as Nu-Serum (Collaborative Research Inc., Lexington, Mass.).

Results of unknown samples will be compared with results obtained from cell which are sensitive to transformation by KiMSV and which will be used as positive controls; cells resistant to transformation by KiMSV which will be used as negative controls.

6. Example: CANCER SUSCEPTIBILITY

The following examples serve to illustrate the nature of the invention without being a limitation of the scope thereof.

6.1. SKIN BIOPSY SOURCES

Skin fibroblasts (SF) from patients exhibiting the generally accepted clinical criteria for the autosomal dominant traits adenomatosis of the colon and rectum (ACR), and neurofibromatosis (NF) and individuals without clinically apparent disease were included in this study. In addition, control individuals whose history and physical examination did not reveal any familial disorders or cancer were examined.

6.2. SKIN FIBROBLAST CULTURES

Subepidermoid biopsy specimens (approximately 1–2 mm$^2$) were taken from normal-appearing flat skin from the lateral aspect of the forearm of human volunteers. Human SF cultures were established from these specimens as follows. The skin biopsies were transferred into a cell culture dish and minced to small pieces with a sharp surgical scalpel (primary explants). The explants (about 4 or 5 pieces) were placed into plastic petri dishes (60 mm in diameter) and maintained in growth medium consisting of Eagle's minimal essential medium (EMEM) with Earle's balanced salt solution (GIBCO Laboratories, Grand Island, N.Y.), supplemented with 2mM glutamine, (GIBCO Laboratories, Grand Island, NY) and penicillin, (100 U/ml, (GIBCO Laboratories), NY) and streptomycin (100 μg/ml, Eli Lilly Company, Indianapolis, IN), 1% sodium pyruvate and 1x nonessential amino acids (GIBCO Laboratories, Grand Island, NY) and 20 percent (w/v) fetal bovine serum (FBS). The culture dishes were incubated at 37° C. in a 5 percent $CO_2$, 95 percent air atmosphere and the medium was changed every three to four days. Confluent cell cultures from these explants, were removed with an ethylenediaminetetracetic acid (EDTA)/trypsin mixture, subcultured in EMEM in the presence of 10% FBS and used within the first 5 to 10 passages (4–6 weeks) in culture for viral transformation assays. All cell preparations were monitored to exclude mycoplasma and bacterial contaminants. A portion of these cultures were stored in liquid nitrogen for future use.

6.3. PREPARATION OF KIRSTEN MURINE SARCOMA VIRUS (KiMSV)

KiMSV stocks were propogated and plaque purified in a normal rat kidney cell line, NRK (Klement et al., 1971, J. Nat. Cancer Inst. 47:65–73). NRK cells were transformed in vitro by KiMSV and tissue culture fluid from these cells was harvested 24 and 48 hours after plating. Alternatively, already transformed tNRK cell cultures were used to harvest virus. For efficient production of virus it is imperative to maintain the cultures of transformed NRK cells at a low volume of medium to surface area, e.g., 40–80 ml culture medium 840–850 cm$^2$ total area in the presence of 2 μg/ml hydrocortisone. Rotating bottles placed on rotating platforms may be used. The tissue culture fluid was clarified by low speed centrifugation in a bench top Fisher centrifuge at about 2500 revolutions per minute at 4° C. for 10 minutes and stored in liquid nitrogen for future use. A single standard pool of KiMSV was used in all viral transformation assays. The virus stock was assayed for focus formation on rat NRK cells, and the titer was expressed as focus-forming units/ml as described by Hartley and Rowe (1966, Proc. Nat. Acad. Sci. USA 55: 780–786).

6.4 VIRAL INFECTION

Cells were plated at a density of 4000 cells/cm$^2$ in Costar (Cambridge, Mass.) six well trays (total area of one well is 9.5 cm$^2$) 24 hours prior to infection with virus. The virus preparation was freshly thawed for each experiment and was passed through a 0.22μ filter (GIBCO, Grand Island, N.Y.) immediately prior to cell infection. The cultures were treated for one hour with DEAE-dextran (molecular-weight >2 ×10$^6$ daltons, Pharmacia Fine Chemicals Piscataway, N.J.) at a final concentration 25 μg/ml in a total incubation volume of two ml. The cultures were then inoculated with 0.2 ml of appropriately diluted (serial 10-fold dilutions) of the freshly thawed and filtered KiMSV stock for one hour, followed by a media change in the presence of 500 ng/ml hydrocortisone (HC, 11 β,17α,21-Trihydroxypregn-4-ene-3, 20-dione, Sigma Chemicals, St. Louis, Mich.) Cultures were maintained for 14–21 days at 37° C. in an atmosphere of 5% $CO_2$/95% air during which time the medium, containing 500 ng/ml of hydrocortisone, was changed approximately every 3 days.

The total number of transformed foci and enzyme levels were determined at 14–21 days post-infection.

6.5 TRANSFORMATION ASSAY

The cultures were observed after transformation and addition of the glucocorticoid hydrocortisone (See FIG. 1). Cells in culture were first stained with Oil-Red-O (Pairoult and Green, 1979, Proc. Natl. Acad. Sci USA 76: 5138–5142) which is specific for triglyceride containing droplets. Oil-Red-O is, therefore, used to identify fully mature fat cells. The cells were fixed by removing the media and inverting the petri dish on top of a 0.45μ filter (Millipore Corporation, Lexington, Mass.) previously soaked in 10% buffered formaldehyde. The cells were exposed to the formaldehyde vapors for 15–30 minutes at room temperature and then stained with Oil-Red-O for 3 hours (Rowley Biochemicals Inst., Rowley, Mass.). This procedure was followed by a wash with 60% ethanol fixation by methanol/Giemsa staining. The total number of foci, including both converted and non-converted to fat cell, was determined, by counting. As illustrated in FIG. 1A the addition of hydrocortisone to cultures following viral infection produced the transformed/neodifferentiated fat cell phenotype in which the cytoplasm was reduced to a thin film surrounding a few very large fat droplets.

6.6. MEASUREMENT OF GLYCEROPHOSPHATE DEHYDROGENASE AS A TRANSFORMATION/NEODIFFERENTIATION MARKER

The conversion of the KiMsV transformed skin fibroblasts in cell cultures containing hydrocortisone was examined by the measurement of the lipogenic enzyme glycerophophate dehydrogenase (GDH). This enzyme plays an important role in triglyceride synthesis and increases during the transformation/neodifferentiation of SF to fat cells.

After 17 days the cultures were washed twice with isotonic phosphate buffer saline (calcium, magnesium-free) and removed by scraping with a rubber policeman into 50 mM Tris buffer (pH 7.5) containing 1 mM EDTA and 1 mM β-mercaptoethanol. The cell suspensions were then treated for 5 seconds at 40 watts with the microtip of a Branson model 185 Sonifier (Ultrasound, Long Island, N.Y.). After centrifugation at 800×g for 5 minutes at 4° C. to remove cell nuclei, the supernatant fractions were centrifuged for one hour at 100,000× g at 4° C. The supernatant fractions were assayed for glycerophosphate dehydrogenase activity.

The enzyme assay was performed essentially according to Kopelovich et al. (1966, Cancer Research 26:1534–1546) as modified by Wise and Green (1979, J. Biol. Chem. 254:273–275). The standard mixture contained 100 mM triethanolamine-HCl buffer, 2.5 mM EDTA, 0.12 mM NADH, 0.2 mM dihydroxyacetone phosphate, 0.1 mM β-mercaptoethanol and varying amounts of cell extract in a final volume of 1.0 ml. The change in absorbance at 340 nm was followed with a Gilford 250 recording spectrophotometer (Gilford Instruments, Chicago, Ill.) at 25° C. One unit of enzyme activity corresponds to the oxidation of 1 nmole of NADH/minute.

A preliminary virus titration assay was conducted to determine the kinetics of GDH with virus infection. Table I describes the results obtained using various dilutions of stock virus. The experiment shows that the level of GDH was indeed directly proportional to both the virus titer and total number of foci formed.

TABLE I
MEASUREMENT OF GDH IN A VIRUS TITRATION EXPERIMENT[a]

| Dilutions of stock virus[b] | Foci formed | Virus titer FFU/ml | Log Virus Titer | GPD nmoles/min/ mg protein |
|---|---|---|---|---|
| $1 \times 10^{-3}$ | TC >100 | $>5.0 \times 10^5$ | >5.69 | 1469 (1275–1622) |
| $1 \times 10^{-4}$ | 12.0 (9–15) | $6.5 \times 10^5$ | 5.81 | 138 (112–169) |
| $1 \times 10^{-5}$ | 1.6 (0–4) | $8.0 \times 10^5$ | 5.9 | 12 (4–17) |
| no virus added | 0 | NA[d] | NA[d] | 2.02 (0–4) |

[a]Skin fibroblasts from an ACR individual were plated as described in the text. After 24 hours the cells were infected with various dilutions of the virus followed by a media change in the presence of 500 ng/ml hydrocortisone. The transformed foci and enzyme levels were determined on about day 17 post infection. Numbers in parentheses denote a range.
[b]Virus titer represents the number of foci forming units (FFU) per one ml of undiluted virus.
[c]TC denotes too many foci to count, in which case the number of foci represents an approximation.
[d]NA denotes not applicable.

The level of the enzyme GDH was measured for individuals of various genotypes as described in Table II. Cells strains which are known to be sensitive to transformation by KiMsV and those which are known to be resistant to such transformation were used as positive and negative controls. The results indicate that virally infected SF of individuals with autosomal dominant traits and an individual from a family with an extensive history of cancer produce higher levels of GDH than normal individuals.

TABLE II
MEASUREMENT OF GDH IN KiMsV TRANSFORMED HUMAN SKIN FIBROBLASTS[a]

| Geno- types[b] | Dilution of Stock Virus | Foci Formed | Virus Titer (FFU/ml) | Log Virus Titer | GPD nmoles/min mg/protein |
|---|---|---|---|---|---|
| N | $1 \times 10^{-2}$ | 3.4 (2–6) | $1.7 \times 10^3$ | 3.23 | 31 (19–40) |
|   | $1 \times 10^{-4}$ | 0 | 0 | 0 | 2.6 (1.2–5) |
| N | $1 \times 10^{-2}$ | 1.8 (1–3) | $9.0 \times 10^3$ | 3.95 | 12.3 (9–18) |
|   | $1 \times 10^{-4}$ | 0 | 0 | 0 | 1.7 (1.5–2.7) |
| N* | $1 \times 10^{-2}$ | TC | — | — | 1973 (1560–2200) |
|   | $1 \times 10^{-4}$ | 20.4 (15–28) | $1.0 \times 10^6$ | 6.00 | 240 (218–258) |
| ACR | $1 \times 10^{-2}$ | TC | — | — | — |
|   | $1 \times 10^{-4}$ | 11.4 (7–18) | $5.5 \times 10^5$ | 5.74 | 113.8 (96–132) |
| NF | $1 \times 10^{-2}$ | TC | — | — | — |
|   | $1 \times 10^{-4}$ | 3.8 (2–6) | $1.9 \times 10^5$ | 5.27 | 39.8 (31–46) |

[a]Skin fibroblasts were treated as described in Table I.
[b]Genotypes are designated as follows: N is a normal individual; N* is a 30 year old female clinically-free of any cancer-associated symptoms, but whose family has an extensive history of leukemia; ACR is an individual with adenomatosis of the colon and rectum; NF is an individual who has neurofibromtosis. The latter two individuals have been previously shown to be highly sensitive to transformation by KiMSV. See Table I for further details.

What is claimed is:

1. A method for a viral transformation assay for determining predisposition of humans to cancer comprising:
   (a) obtaining a skin biopsy specimen from a human subject;
   (b) establishing a human skin fibroblast culture from the skin biopsy specimen;
   (c) incubating the human skin fibroblast culture in a growth and maintenance medium at 37° C. for an amount of time sufficient to establish monolayer cultures;
   (d) treating the cell cultures with DEAE-dextran;
   (e) infecting the resultant human skin fibroblast cultures with Kirsten murine sarcoma virus;
   (f) exposing the cultures to the medium supplemented with an effective amount of a glucocorticosteroid hormone; and
   (g) measuring the level of a lipogenic enzyme in such cultures to monitor the extent of transformation/neodifferentiation.

2. The method for an improved viral transformation assay according to claim 1, wherein the skin biopsy specimen is a subepidermoid biopsy specimen.

3. The method for an improved viral transformation assay according to claim 1, wherein the glucocorticosteroid hormone is hydrocortisone.

4. The method for an improved viral transformation assay according to claim 1, wherein the glucocorticosteroid hormone is hydrocortisone 21-acetate.

5. The method for an improved viral transformation assay according to claim 1, wherein the glucocorticosteroid hormone is hydrocortisone 21-hemisuccinate.

6. The method for an improved viral transformation assay according to claim 1, wherein the glucocorticosteroid hormone is dexamethasone.

7. The method for an improved viral transformation assay according to claim 1, wherein the growth and maintenance medium contains an artificial serum.

8. The method for an improved viral transformation assay according to claim 1, wherein the lipogenic enzyme is α-glycerophosphate dehydrogenase, glucose-6-phosphate dehydrogenase, malic enzyme, citrate cleavage enzyme, acetyl-CoA carboxylase or fatty acid synthetase.

9. The method for an improved viral transformation assay according to claim 1, wherein the lipogenic enzyme is glycerophosphate dehydrogenase.

10. A method for a viral transformation assay for determining predisposition in humans to cancer comprising:
    (a) obtaining a subepidermoid skin biopsy specimen;
    (b) establishing a human skin fibroblast culture from the subepidermoid biopsy specimen;
    (c) incubating the humar skin fibroblast culture in a growth and maintenance medium at 37° C. for an amount of time suffcient to establish monolayer cultures;
    (d) treating the cell cultures with DEAE-dextran;
    (e) infecting the resultant human skin fibroblast cultures with Kirsten murine sarcoma virus;
    (f) maintaining such cultures in the medium supplemented with hydrocortisone at a concentration of about 100-1000 ng/ml; and
    (g) measuring the level of a lipogenic enzyme in such culture to monitor the extent of transformation/neodifferentiation.

11. The method for an improved viral transformation assay according to claim 10, wherein the growth and maintenance medium contains an artificial serum.

12. The method for an improved viral transformation assay according to claim 10, wherein the lipogenic enzyme is α-glycerophosphate dehydrogenase, glucose-6-phosphate, malic enzyme, citrate cleavage enzyme, acetyl-CoA carboxylase or fatty acid synthase.

13. The method for an improved viral transformation assay according to claim 11, wherein the lipogenic enzyme is α-glycerophosphate dehydrogenase.

* * * * *